US007619119B2

(12) United States Patent
Arredondo et al.

(10) Patent No.: US 7,619,119 B2
(45) Date of Patent: *Nov. 17, 2009

(54) PROCESSES FOR CONVERTING GLYCEROL TO AMINO ALCOHOLS

(75) Inventors: Victor Manuel Arredondo, West Chester, OH (US); Patrick Joseph Corrigan, Glendale, OH (US); Angella Christine Cearley, Hamilton, OH (US); Deborah Jean Back, Cleves, OH (US); Michael Steven Gibson, Cincinnati, OH (US); Neil Thomas Fairweather, Liberty, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 217 days.

This patent is subject to a terminal disclaimer.

(21) Appl. No.: 11/810,778

(22) Filed: Jun. 7, 2007

(65) Prior Publication Data
US 2007/0287868 A1  Dec. 13, 2007

Related U.S. Application Data

(60) Provisional application No. 60/811,704, filed on Jun. 7, 2006.

(51) Int. Cl.
C07C 209/24 (2006.01)
C07C 209/26 (2006.01)
C07C 209/28 (2006.01)

(52) U.S. Cl. .................. 564/471; 564/463; 564/472

(58) Field of Classification Search .............. None
See application file for complete search history.

(56) References Cited

U.S. PATENT DOCUMENTS

| 3,448,153 A | 6/1969 | Cavitt |
| 4,105,669 A | 8/1978 | Himmele et al. |
| 4,111,840 A | 9/1978 | Best |
| 4,123,462 A | 10/1978 | Best |
| 4,151,204 A | 4/1979 | Ichikawa et al. |
| 4,642,394 A | 2/1987 | Che |
| 4,942,266 A | 7/1990 | Fleckenstein et al. |
| 4,982,020 A | 1/1991 | Carduck et al. |
| 5,081,321 A | 1/1992 | Fukuhara et al. |
| 5,214,219 A | 5/1993 | Casale et al. |
| 5,276,181 A | 1/1994 | Casale et al. |
| 5,288,911 A | 2/1994 | Koppenhoefer et al. |
| 5,364,986 A | 11/1994 | Demmering et al. |
| 5,387,720 A | 2/1995 | Neher et al. |
| 5,426,249 A | 6/1995 | Haas et al. |
| 5,536,879 A | 7/1996 | Antons et al. |
| 5,616,817 A | 4/1997 | Schuster et al. |
| 5,731,479 A | 3/1998 | Antons |
| 6,057,442 A | 5/2000 | Wulff-Doring et al. |
| 6,080,898 A | 6/2000 | Drent et al. |
| 6,310,254 B1 | 10/2001 | Antons et al. |
| 6,376,713 B1 | 4/2002 | Baiker et al. |
| 6,479,713 B1 | 11/2002 | Werpy et al. |
| 6,841,085 B2 | 1/2005 | Werpy et al. |
| 2005/0244312 A1 | 11/2005 | Suppes et al. |

FOREIGN PATENT DOCUMENTS

| CS | 209151 B1 | 11/1981 |
| DE | 41 28 692 A1 | 3/1993 |
| DE | 4128692 A1 * | 3/1993 |
| DE | 43 02 464 A1 | 8/1994 |
| GB | 1 554 176 | 10/1979 |
| JP | 01056662 | 3/1989 |
| WO | WO 93/05006 | 3/1993 |
| WO | WO 2005/095536 A2 | 10/2005 |
| WO | WO 2007/010299 A1 | 1/2007 |

OTHER PUBLICATIONS

Abaco, Atsushi et al., "An Improved, Convenient Procedure for Reduction of Amino Acids to Aminoalcohols: Use of NaBH4-H2SO4," Tetrahedron Letters, 1992, vol. 33, No. 38, pp. 5517-5518.

Carberry, James, "Chemical and Catalytic Reaction Engineering," Dover Publications Inc., Mineola NY, 1973, pp. 406 and 520.

Chiu, Chuang-Wei et al., "Dehydration of Glycerol to Acetol via Catalystic Reactive Distillation," AIChE Journal, 2006, vol. 52, No. 10, pp. 3543-3548.

Dasari, Mohanprasad et al., "Low Pressure Hydrogenolysis of Glycerol to Propylene Glycol," Applied Catalysis A: General, 2005, vol. 28, pp. 225-231.

Gobolos, S., et al., "Reductive Amination of Acetone on Tin Modified Skeletal Nickel Catalysts," Heterogeneous Catalysis and Fine Chemicals II, Elsevier Science Publication, 1991, pp. 335-342.

Gomez, Silvia, et al., "The Reduction Amination of Aldehydes and Ketones and the Hydrogenation of Nitriles: Mechanistic Aspects and Selectivity Control," Adv. Synth. Catal., 2002, vol. 344, No. 10, pp. 1037-1057.

Gribble, Gordon W., et al., "Sodium Borohydride in Carboxylic Acid Media: A Phenomenal Reduction System," Chemical Society Reviews, 1998, vol. 27, pp. 395-404.

(Continued)

Primary Examiner—Brian J Davis
(74) Attorney, Agent, or Firm—Stephen T. Murphy; Kim William Zerby; Steven W. Miller

(57) ABSTRACT

Processes for converting glycerol to an amino alcohol product involving reacting glycerol with a metal catalyst to obtain hydroxyacetone, and reacting the hydroxyacetone with an amine compound to obtain an adduct that is then reduced using a reducing agent to obtain an amino alcohol product are described.

23 Claims, 2 Drawing Sheets

OTHER PUBLICATIONS

Jere, Frank T., et al., "Stereoretentivie C-H Bond Activation in the Aqueous Phase Catalytic Hydrogenation of Amino Alcohols," Organic Letters, 2003, vol. 5, No. 4, pp. 527-530.

McKennon, Marc J., et al., "A Convenient Reduction of Amino Acids and Their Derivatives," Journal of Organic Chemistry, 1993, vol. 58, pp. 3568-3571.

Nishimura et al., "Handbook of Heterogeneous Catalytic Hydrogenation for Organic Synthesis," Wiley & Sons, 2001, Chapter 6, pp. 226-253.

Nishimura et al., "Handbook of Heterogeneous Catalytic Hydrogenation for Organic Synthesis," Wiley & Sons, 2001, Chapter 8, pp. 286-314.

* cited by examiner

PROCESSES FOR CONVERTING GLYCEROL TO AMINO ALCOHOLS

CROSS REFERENCE TO RELATED APPLICATION

This application claims the benefit of U.S. Provisional Application No. 60/811,704, filed Jun. 7, 2006, the disclosure of which is incorporated in its entirety by reference herein.

FIELD OF THE INVENTION

Embodiments described herein relate generally to processes for producing amino alcohols from glycerol.

BACKGROUND OF THE INVENTION

Some amino alcohols may be represented by the general formula:

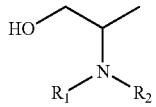

These amino alcohols can be valuable materials because they may be used as solvents, intermediates for making surface active agents, corrosion inhibitors in metal working fluids, neutralizing agents in acid scrubbing during natural gas or syngas purification processes, and aids in the preparation of compounds for use in the pharmaceutical industry.

Currently, processes exist for the preparation of amino alcohols. Such processes can involve reacting polyhydroxy compounds, such as ethylene glycol, 1,2-diols, 1,3-diols, and polyglycols, with amine compounds and hydrogen in the presence of a heterogeneous catalyst. One concern with such processes is that they can exhibit poor-to-moderate conversions and selectivities. This undesired outcome can result from the fact that the reactions can yield complex product mixtures consisting of amino alcohols, di-and tri-amines, oligomeric polyamines, cyclic amines (e.g. pyrrolidines, piperidines, and piperazines), unreacted starting materials and other unidentified compounds. Examples of these catalysts and processes can be found in U.S. Pat. Nos. 6,376,713; 6,057,442; 5,288,911; 4,123,462; 4,151,204; and 4,111,840.

Alternately, amino alcohols can be prepared by reacting an amine compound with 2-chloro-1-propanol (see, for example, JP 01056652) or by stoichiometric reduction of the corresponding amino acids and ester derivatives with a variety of reducing reagents (A. Abiko et al., Tetrahedron Lett. 1992, 33, 5517; M. J. McKennon, et al., J. Org. Chem. 1993, 58, 3568, and references therein) and by catalytic hydrogenation of amino acids, for example as reported in U.S. Pat. Nos. 5,536,879; 5,731,479; and 6,310,254. In works described by Miller, et al., (Organic Letters, 2003, 5(4), 527) on the conversion of alanine to desired products it is stressed the importance of performing hydrogenations at low pH such that the amino acid is in the protonated form rather than carboxylate form. In general, the catalytic hydrogenation of amino acids require a low solution pH in conjunction with high catalyst loading, prolonged reaction times, and high hydrogen pressure. Thus, these processes can often be costly since additional expensive feedstocks and reagents are needed.

Therefore, there remains a need for processes for making amino alcohols from inexpensive feedstocks, such as crude glycerol, which can also reduce or eliminate the production of substantial amounts of undesired byproducts.

SUMMARY OF THE INVENTION

Embodiments of the present disclosure generally relate to processes for producing amino alcohols from glycerol.

In one exemplary embodiment, process of the present disclosure generally relate to reacting glycerol with a metal catalyst to obtain hydroxyacetone, reacting the hydroxyacetone with an amine compound to obtain an adduct; and reducing the adduct using a reducing agent to obtain an amino alcohol product.

In another exemplary embodiment, processes of the present disclosure generally relate to reacting glycerol with a metal catalyst at a temperature of from about 160° C. to about 300° C. to obtain hydroxyacetone, reacting the hydroxyacetone with an amine compound at a temperature of from about −20° C. to about 150° C. to obtain an adduct, and reducing the adduct using a reducing agent at a temperature of from about 20° C. to about 250° C. to obtain an amino alcohol product.

In yet another exemplary embodiment, processes of the present disclosure generally relate to converting glycerol to an amino alcohol having the formula:

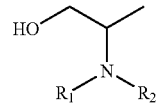

the process comprising reacting glycerol with a metal catalyst at a temperature of from about 160° C. to about 300° C. to obtain hydroxyacetone, reacting the hydroxyacetone with an amine compound at a temperature of from about −20° C. to about 150° C. to obtain an adduct, and reducing the adduct using a reducing agent at a temperature of from about 20° C. to about 250° C. to obtain an amino alcohol product wherein $R_1$ and $R_2$ are independent of one another and are selected from the group consisting of H, $C_1$-$C_{20}$ alkyl, $C_3$-$C_{20}$ cycloalkyl, $C_1$-$C_{20}$ hydroxyalkyli, aryl, $C_7$-$C_{20}$ alkyl-aryl, $C_7$-$C_{20}$ aryl-alkyl, and mixtures thereof, or $R_1$ and $R_2$ come together with the nitrogen to form a heterocyclic ring having from 5 to 7 ring atoms.

BRIEF DESCRIPTION OF THE DRAWINGS

It is believed that the Description of the Invention will be better understood with reference to the following drawings, wherein.

DETAILED DESCRIPTION OF THE INVENTION

A. Definitions

Figure 1:
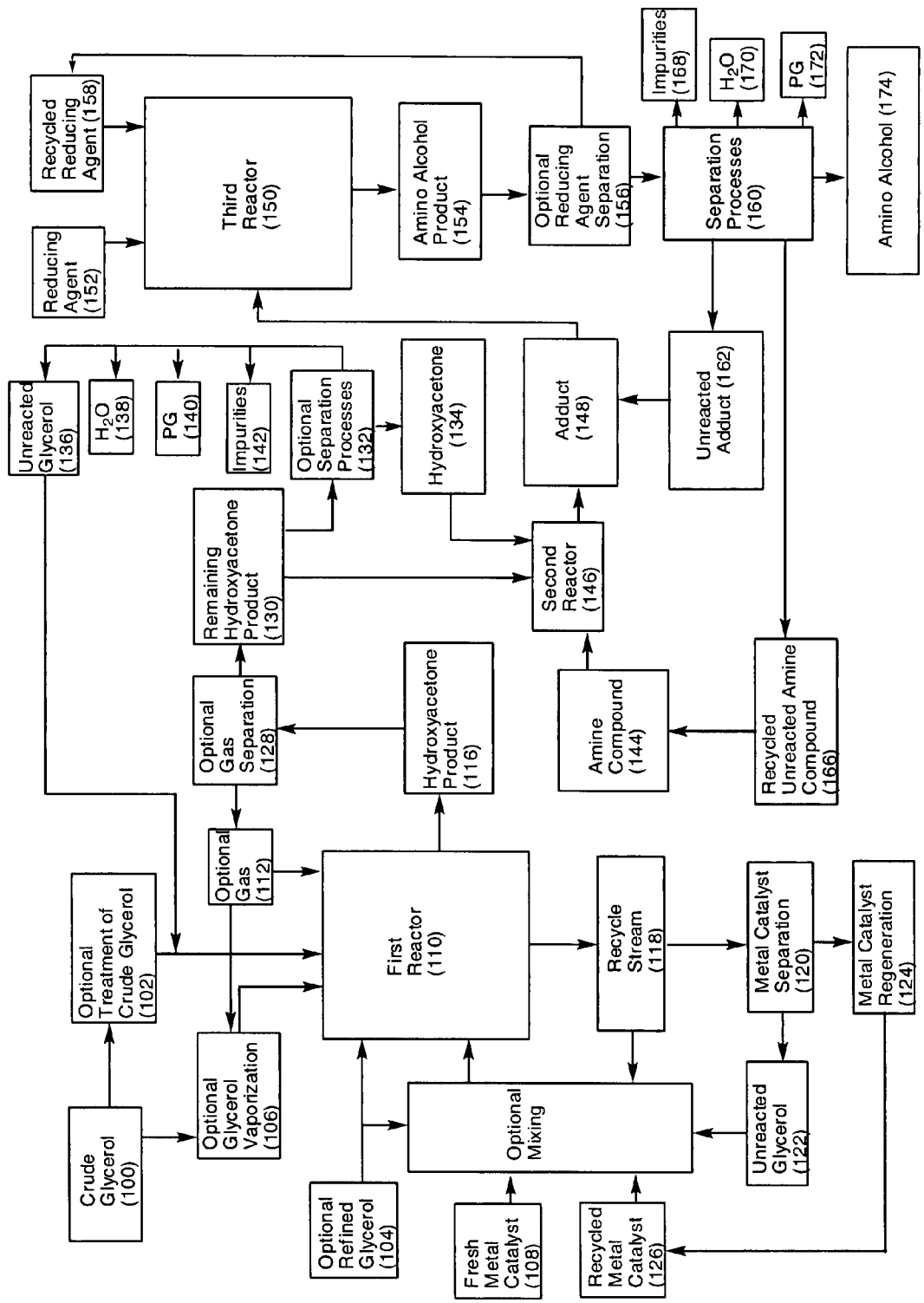
FIG. 1 is a schematic flowchart representing an exemplary embodiment of a multiple stage process in accordance with the present disclosure.

As used herein, "comprising" means the various components, ingredients, or steps, which can be conjointly employed in practicing various embodiments of the present disclosure. Accordingly, the term "comprising" encompasses the more restrictive terms "consisting essentially of" and "consisting of."

As used herein, "adduct" means any chemical species formed by the combination or condensation of two or more substances, such as hydroxyacetone and an amine compound.

As used herein, "crude glycerol" refers to glycerol that may contain impurities, including, but not limited to, water, inorganic salts such as chloride, sulfate, phosphate, acetate salts and others, organic compounds such as fatty acids, fatty esters, mono-glycerides, di-glycerides, phospholipids, protein residues, methanol, acids, bases or combinations of any thereof. Impurities may account for from about 10% to about 50% of the crude glycerol, by weight.

As used herein, "reaction components" generally refers to chemical species that take part in a chemical transformation, for example, but not limited to, solvents, reactants, and catalysts. In addition, "reaction components" may include a gas, liquid, or solid or a reaction component dissolved in a solvent.

As used herein, "reducing agent" refers to any element, compound, or combination of elements and/or compounds that reduces another species by either increasing the hydrogen content or decreasing the oxygen content of the other species.

As used herein, the term "RANEY®" when used in conjunction with a metal catalyst means a catalyst that has been treated by a process that activates the catalyst, such as by reacting the catalyst with a second metal, such as aluminum, and/or by increasing the surface area of the catalyst. For example a RANEY® metal is a solid catalyst composed of fine grains of a metal-aluminum allow, produced when a block of the alloy is treated with concentrated sodium hydroxide to activate the catalyst. The activated catalyst has a porous structure with a high surface area. RANEY® is a registered trademark of W.R. Grace and Company, New York, N.Y. Other suitable catalysts that may be used in place of a RANEY® catalyst include skeletal catalysts and/or sponge metal catalysts.

As used herein, the term "glycerol" may refer to any of crude, treated, or refined glycerol as described herein, unless the glycerol is specifically designated as being crude, treated, or refined.

As used herein, the term "refined glycerol" means glycerol that is at least about 99% pure (i.e. containing less than about 1% impurities, such as those impurities described herein).

As used herein, the term "treated glycerol" means glycerol that has undergone at least one treating process such that the treated glycerol comprises greater than about 1% to about 10% impurities, such as those impurities described herein.

As used herein, "treating" means removing at least a portion of the impurities from the crude glycerol. "Treating" may be accomplished by a variety of methods, including, but not limited to neutralization, precipitation, filtration, evaporation, steam stripping, ion-exchange, adsorption, membrane separation, such as microfiltration, nanofiltration, osmosis and reverse osmosis, electro-deionization, and combinations of any thereof.

All percentages are by weight unless otherwise specified.

B. Processes

Embodiments described herein relate generally to two-step processes for producing amino alcohols from glycerol. More specifically, embodiments herein disclose two-step processes for catalytically converting glycerol to hydroxyacetone in a first step and hydroxyacetone to an amino alcohol in a second step, as represented by the following:

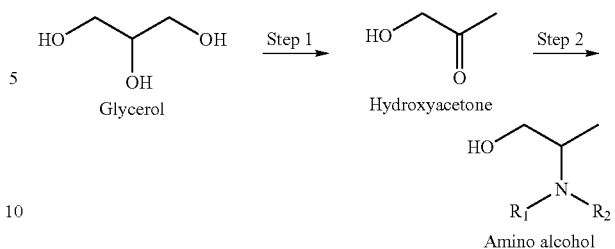

According to other embodiments, the process may be a one step process in which the conversion of glycerol to hydroxyacetone and the conversion of the hydroxyacetone to the amino alcohol may occur in a single reaction process (one-pot or single reactor). Variations of such processes will become clear from the following description.

According to various embodiments, the processes herein involve reacting glycerol with a metal catalyst to obtain hydroxyacetone. According to certain embodiments, the hydroxyacetone product may further comprise other components, such as, for example, any of unreacted glycerol, water, propylene glycol and other impurities. Glycerol acceptable for use herein may be liquid crude, treated or refined glycerol, or crude glycerol vapor, as described in greater detail herein. Referring to FIG. 1 throughout, crude glycerol (100) may contain impurities, including, but not limited to, water, inorganic salts such as chloride, sulfate, phosphate, acetate salts and others, organic compounds such as fatty acids, fatty ester, mono-glycerides, di-glycerides, phospholipids, protein residues, methanol, acids, bases and combinations of any thereof. In certain embodiments, of the crude glycerol, impurities may account for at least about 10% of the crude glycerol, and in specific embodiments from about 10% to about 50% of the crude glycerol, by weight. In other embodiments, the crude glycerol may comprise less than 10% impurities, such as from 1% to 10% impurities. It will be understood by one skilled in the art that the amount of impurities in the crude glycerol may vary according to the method of production and that in certain more efficient processes, the crude, untreated, glycerol may contain lower levels of impurities that the crude glycerol from other processes. The purity of the "crude" glycerol used in the reaction should not be viewed as limiting herein. According to certain embodiments, the crude glycerol may be obtained in the course of the production of biodiesel, or from the conversion of fats/oils of plant or animal origin through saponification, trans-esterification or hydrolysis reactions. As described herein, in certain conventional processes, crude glycerol must first be refined prior to use in order to facilitate process control, maximize process yields, avoid catalyst poisoning, and/or reduce impurities in the final reaction product. Because such refining processes can be costly, in certain embodiments of the processes herein, it may be more desirable to use the crude glycerol directly or with minimal processing, treating, or purification. Various embodiments described herein may address this issue by providing more cost-effective processes that allow for the use of crude glycerol without refinement or treating the glycerol.

Although embodiments of the present disclosure generally focus on the use of crude glycerol, the processes of the present disclosure are not limited to the use of crude glycerol. For example, in another embodiment, crude glycerol may be optionally treated (102) prior to use in the processes described herein. Treating the crude glycerol can aid in reducing the amount of impurities present without having to fully refine the crude glycerol. In this way, treating the crude glycerol can result in significant cost savings compared to refinement. As used herein, "treating," crude glycerol may be accomplished by a variety of methods, including, but not limited to neutralization, precipitation, filtration, evaporation, steam stripping, ion-exchange, adsorption, membrane separation, such as microfiltration, nanofiltration, osmosis and reverse osmosis, electro-deionization, and combinations of any thereof. Those skilled in the art will understand how the treatment of crude glycerol can be accomplished via the various methods set forth above, and that such treatment may vary depending on the impurities present. Regardless of which treatment method is employed, the resulting "treated glycerol" may comprise from about 1% to about 10% of the aforementioned impurities by weight. The reduction in impurities in the treated glycerol may help provide better reaction yields in the processes described herein.

According to other embodiments, refined glycerol (104) having greater than about 99% purity may also be acceptable for use herein. The glycerol may be refined according to any refinement method known in the art. In various embodiments, the refined, treated, or crude glycerol may be neat or diluted with a polar solvent (e.g. water or an alcohol). Various mixtures of refined, treated and/or crude glycerol may also be suitable for use in various embodiments disclosed herein.

Alternately, according to other embodiments, the crude glycerol may be vaporized (106) prior to submitting the glycerol to the processes described herein. As vapor phase reactions can be faster than liquid phase reactions, glycerol vapor may be desired such that the first portion of the process may be conducted in the vapor phase, for example, to speed up the rate of the reaction. Glycerol vaporization may be carried out using any vaporizer known to those skilled in the art including, but not limited to, a flash tank evaporator or a wiped film evaporator. One skilled in the art would recognize that the conditions of temperature and pressure may vary according to the vaporization equipment used. An additional benefit of vaporizing the crude glycerol is that glycerol vaporization may reduce the amount of impurities present in the crude glycerol without having to fully refine the glycerol. In this way, using glycerol vapor may be a more cost effective option than using refined glycerol. As used herein, the term "glycerol" shall include crude, treated, or refined glycerol except where specifically designated as specifically crude, treated or refined.

A metal catalyst (108) may also be provided to react with the glycerol to produce hydroxyacetone. According to various embodiments, any metal catalyst having active sites comprising one or more transition element metals may be used herein. For example, according to certain embodiments, the metal catalyst may include, but are not limited to, copper, chromium, nickel, zinc, cobalt, manganese, silicon, aluminum, oxides thereof and combinations of any thereof. According to one embodiment, the metal catalyst may be a copper chromite catalyst (also known in the art as a copper-chromium oxide catalyst) that may comprise from about 15% to about 75% copper oxide and from about 20% to about 75% chromium trioxide. According to another embodiment the catalyst may be a "chrome-free" copper catalyst, such as a copper zinc catalyst or a copper oxide catalyst. Chrome-free copper catalysts may exhibit comparable or superior activity and selectivity to conventional copper chromite catalysts for certain reactions and eliminate the environmental issues associated with the disposal of chrome-containing catalysts. In certain embodiments the chrome-free copper zinc catalyst may comprise from about 20% to about 75% copper oxide, from about 20% to about 60% zinc oxide, and from about 20% to about 70% alumina and in another embodiment the chrome-free copper oxide catalyst may comprise from about 20% to about 80% copper oxide and from about 25% to about 70% alumina. Additionally, the metal catalyst, for example, the copper chromite catalyst or the copper zinc catalyst, may contain small amounts of stabilizers, such as barium oxide. In certain embodiments, the metal catalyst may also be promoted with one or more metal oxides including, but not limited to, magnesium, calcium, barium, manganese, molybdenum or silicon, which may help render the metal catalyst more active and/or more stable. Moreover, in certain embodiments, the metal catalyst may be used fresh (i.e. the oxide form) or it may be reduced in a stream of hydrogen prior to use. According to certain embodiments, the use of a reduced catalyst may be desired for various reasons. For example, in certain embodiments, using a reduced catalyst may produce hydroxyacetone more rapidly and with fewer impurities and, in other embodiments, using a reduced catalyst may contribute to a longer catalyst lifetime due to resistance to catalyst poisoning and/or degradation.

According to various embodiments, reacting the glycerol and the metal catalyst may occur in a first reactor (110), optionally in the presence of a gas (112), in a slurry mode or a fixed bed mode. Any reactor known to those skilled in the art may be used herein and may include a batch reactor, a stirred tank reactor, a semi-batch reactor, a continuous reactor, a continuous stirred tank reactor, a slurry reactor, a fixed bed reactor, a tubular reactor, a column reactor, a packed bed reactor, a fluidized bed reactor, a trickle bed reactor, a membrane reactor, a plate and frame reactor, a Carberry-type reactor (also called the "Notre Dame reactor, see, J. J. Carberry, "Chemical and Catalytic Reaction Engineering," Dover Publications, Inc. Mineola, N.Y., 1976, p. 406, see also p. 520 for an illustration of various reactor types suitable for use in the present disclosure, the disclosure of which in incorporated in its entirety by reference herein), a plug flow reactor, and a reactive distillation, or various combinations of any thereof. It will be understood that the manner in which the glycerol and metal catalyst are fed/added into the reactor can vary depending on the equipment used and the phase of each reaction component. However, in those embodiments in which glycerol vapor is used, one skilled in the art will understand that it may be more advantageous to have the metal catalyst already in place in the first reactor prior to the addition of the glycerol vapor since it may simplify the process of contacting the glycerol vapor with the metal catalyst.

While the amount of metal catalyst may vary, in one embodiment, the amount may be from about 0.01% to about 100%, and in another embodiment from about 0.01% to about 5% by weight, relative to glycerol, for example in a slurry type reactor. For other reactors, such as continuous reactor, for example a fixed bed reactor (including trickle bed reactors), the catalyst loading of the reactor may vary and may depend on the bed reactor design, such as the bed volume of the reactor and/or the reactant flow rate. One skilled in the art will recognize that the amount of metal catalyst used can vary depending on the type of reactor used and the desired speed of the reaction. For instance, faster reactions can be advantageous because they generally allow for the use of more compact reaction equipment and can result in the formation of fewer byproducts, while slower reactions can be advantageous because they can often be carried out using less catalyst, which can lead to lower operating costs. In certain embodiments, where a faster reaction rate may be desired, the amount of metal catalyst may be increased.

According to certain embodiments, reacting the glycerol with the metal catalyst may occur under gas sparging. If a gas (112) is used, any gas known to those skilled in the art may be acceptable for use herein. Examples of gasses that may be useful in certain embodiments of the present processes can include the noble gases (e.g. helium or argon), nitrogen, carbon dioxide, superheated steam, and combinations of any thereof. In certain embodiments, the gas may comprise nitrogen. Without being limited by theory, it is believed that the inclusion of a gas, in combination with the reaction temperature, can be beneficial because it can improve reaction yields and selectivities by reducing contact time between the catalyst and the hydroxyacetone product by continually aiding in the removal of the hydroxyacetone and water from the reaction mixture as a vapor. For example, as the hydroxyacetone product is formed under the reaction conditions and temperature, it may be vaporized and the hydroxyacetone vapor transmitted out of the reactor by the gas stream. This in turn can prevent the hydroxyacetone from further reacting with the metal catalyst and generating undesired byproducts.

According to one specific embodiment, the first reactor (110) may be a trickle bed reactor. The trickle bed reactor may comprise at least one packed column, wherein the column is packed with the metal catalyst. In certain embodiments, the trickle bed reactor may comprise a plurality of columns, such as, for example, from 2 to 10 columns, arranged in series or in parallel. One skilled in the art would recognize that the number of columns in the trickle bed reactor may vary according to the required reaction time, the flow rate of the process, and/or the height, total bed volume, or catalyst loading of the column. In the trickle bed reactor for the conversion of glycerol to hydroxyacetone, the liquid glycerol feed is fed into the reactor at a low flow so that a thin layer of liquid may form over at least a portion of the surface of the metal catalyst particles that are packed into the column. In certain embodiments, the space between the catalyst particles may be fed with the gas (112), such that as the glycerol is converted to the hydroxyacetone product (116), the hydroxyacetone product is volatilized and the hydroxyacetone vapor carried from the reactor by the gas.

Regardless of the manner of introduction of the various reaction components, once inside the first reactor, the glycerol and metal catalyst may react, in the presence of the gas if included, to produce a hydroxyacetone product that, in addition to hydroxyacetone, may comprise any of unreacted glycerol, water, propylene glycol, and other impurities. While not intending to be limited by theory, it is believed that hydroxyacetone may be formed via a combination of dehydrogenation and dehydration reactions. More specifically, glycerol may be first dehydrogenated to glyceraldehyde in equilibrium with its enolic tautomer. The primary hydroxyl group of this enolic tautomer may then interact with the acidic site present in the chromium oxide, thereby catalyzing the loss of water (dehydration) with concomitant rearrangement of the double bond to yield hydroxyacetone. Alternately, a primary hydroxyl group of the glycerol may strongly interact with an acid site on the catalyst to facilitate the loss of water and yield hydroxyacetone via its enolic tautomer.

In view of the above, it will be understood that reaction conditions can vary depending on the particular reaction components (i.e. glycerol, metal catalyst and gas, if present) and reactor type selected. In certain embodiments, reacting the glycerol with the metal catalyst may occur in the first reactor at a temperature of from about 160° C. to about 300° C., and in another embodiment from about 200° C. to about 240° C. According to certain embodiments, reacting the glycerol with the metal catalyst may occur about atmospheric pressure, although pressures above and below atmospheric pressure, for example in one embodiment, pressures from about 0.1 bar to about 60 bar may be used herein and in another embodiment, pressures from about 0.1 bar to about 10 bar, may be used herein. Similarly, the time needed to carry out the reaction can vary depending on the reaction components used, for example, in one embodiment the reaction may be carried out for from about 1 minute to about 24 hours, as measured by the residence time in the reactor, for example when the glycerol is in the liquid phase. In other embodiments where the glycerol is in a vapor phase, the reaction time may be from about 1 second to about 1 hour. Those skilled in the art will understand how to select the proper process parameters based on such factors as the reaction components, reactant phase, and equipment used.

Once the reaction between the glycerol and metal catalyst occurs, a hydroxyacetone product (116), as well as a recycle stream (118) may be obtained. As used herein, "hydroxyacetone product" means the composition(s) resulting from, or remaining after, reacting the glycerol and metal catalyst, optionally in the presence of the inert gas, in the first reactor. While it should not be limited to such, the hydroxyacetone product will generally be in the vapor phase (which, in certain embodiments, may be condensed prior to the next step in the process). In addition to hydroxyacetone, the hydroxyacetone product may comprise any of unreacted glycerol, propylene glycol, water, impurities and combinations of any thereof. The hydroxyacetone product may also comprise any gas (112) if used in the reaction.

The recycle stream (118) may generally be in the liquid phase and may comprise the metal catalyst, unreacted glycerol, as well as high boiling point impurities. In one embodiment, the recycle stream (118) may be recycled back to the first reactor (110) for reuse. In another embodiment, the metal catalyst in the recycle stream (118) may be partially or completely separated (120) and the remaining unreacted glycerol (122) (and any impurities present) may be recycled back to the reactor (110). The metal catalyst may then be regenerated (124), since it may lose some of its activity over time, prior to being recycled (126) to the first reactor for reuse. Optionally, the recycled metal catalyst (126), whether regenerated or not, may be mixed with fresh metal catalyst (108) and/unreacted glycerol (122) being added back into the first reactor (110) to replace at least a portion of the used/removed reaction components.

Similarly, when handling the hydroxyacetone product (116), the gas (if used) may be optionally separated (128) from the remaining hydroxyacetone product (130) and recycled back to the first reactor (110) for reuse. The remaining hydroxyacetone product (130), which as previously mentioned, may include hydroxyacetone, as well as, in certain embodiments, any of unreacted glycerol, water, propylene glycol and impurities such as 1,3-dimethanol-p-dioxane and (2,4-dimethyl-1,3-dixolan-2-yl)methanol may be further separated if desired (132) to isolate the hydroxyacetone (134) from the unreacted glycerol (136), water (138), propylene glycol (140) and impurities (142). Water and impurities may generally be discarded or recycled, while any propylene glycol may be collected for use in other applications and any unreacted glycerol may be recycled back for use as a reaction component while the hydroxyacetone (134) may be added to a second reactor (146) for further processing.

More specifically, the hydroxyacetone (134) and an amine compound (144) may be reacted in a second reactor (146) to obtain an adduct (148). The amine compound (144) may be selected from the group consisting of ammonia, ammonium hydroxide, hydroxylamine, primary amines, secondary amine, alkanolamines and combinations thereof. In one embodiment, the amine compound may be ammonia, while in another embodiment, the amine compound may be ammonium hydroxide. In another embodiment, the amine compound may be hydroxylamine. One having skill in the art, based on the disclosure herein, will understand that selection of the appropriate amine compound will depend on the structure of the desired amino alcohol product. For example, in certain embodiments where a primary amino alcohol product is desired, an amine compound such as ammonia (gaseous or liquid) or ammonium hydroxide would be selected, whereas a secondary amino alcohol product or a tertiary amino alcohol product would utilize a primary amine compound or secondary amine compound, respectively.

In certain embodiments, optionally reacting the hydroxyacetone with the amine compound to obtain the adduct may further comprise optionally adding an acid catalyst to the hydroxyacetone and the amine compound. For example, in certain embodiments, the rate of the reaction between the hydroxyacetone and the amine compound may be increased by addition of an acid catalyst, such as, for example, a Brønsted-Lowry acid, a Lewis Acid, or combinations of any thereof. Those skilled in the art will understand how to select an acid catalyst, such as a solid acid catalyst, based on such factors as equipment and cost parameters. Some exemplary solid acid catalysts acceptable for use herein may include metal oxides or metal mixed oxides of the elements Zr, Ti, Mo, W, Fe, B, Al and Si; zeolites, metal or ammonium salts of mineral acids such as hydrochloric acid, sulfuric acid, nitric acid, phosphoric acid, or organic acids such as formic acid, acetic acid and sulfonic acids; cross-linked sulfonated polystyrene ion exchange resins such as AMBERLYST™ (Rohm & Haas, USA, PA), polyperfluorosulfonic acid resin such as NAFION® (Dupont, USA, Delaware), with or without silica nanocomposite; kieselguhr, alumina, titania or clays impregnated with a strong acid. While not intending to be limited by any particular mechanism, it is believed that the acid catalyst may activate the carbonyl of the hydroxyacetone toward nucleophilic attack by the amine compound. The acid catalyst may be added to the hydroxyacetone prior to, concomitant with, or after the addition of the amine compound. In another embodiment, a mixture of the hydroxyacetone and the amine compound may be passed over or through an acidic resin. In other embodiments, acid catalysis may not be necessary since the amine compound may directly react with the hydroxyacetone to produce the adduct.

The second reactor (146) may be any reactor known to those skilled in the art including, but not limited to, batch reactor, a stirred tank reactor, a semi-batch reactor, a continuous reactor, a continuous stirred tank reactor, a slurry reactor, a fixed bed reactor, a tubular reactor, a column reactor, a packed bed reactor, a fluidized bed reactor, a trickle bed reactor, a membrane reactor, a plate and frame reactor, a Carberry-type reactor, a plug flow reactor, and a reactive distillation, or various combinations of any thereof. It will be understood that the manner in which the hydroxyacetone and the amine compound are fed/added into the reactor can vary depending on the equipment used and the phase of each reaction component.

In one embodiment, the second reactor (146) is a trickle bed reactor. The trickle bed reactor may comprise at least one packed column, wherein the column is packed with the hydrogenation catalyst. In certain embodiments, the trickle bed reactor may comprise a plurality of columns packed with the hydrogenation catalyst, such as, for example, from 2 to 10 columns, arranged in series or in parallel. One skilled in the art would recognize that the number of columns in the trickle bed reactor may vary according to the required reaction time, the flow rate of the process, and/or the height, total bed volume, or catalyst loading of the column.

The reaction between the hydroxyacetone and the amine compound may be generally carried out at a temperature of from about −20° C. to about 150° C., and in one embodiment from about −10° C. to about 30° C. In certain embodiments, reacting the hydroxyacetone with the amine compound may occur at pressures of from about 1 bar to about 200 bar, and in one embodiment from about 1 bar to about 100 bar. The amine compound may be in excess, with the molar ratio of the amine compound to hydroxyacetone being from about 1:1 to about 10:1, and in one embodiment from about 2:1 to about 4:1. The reaction may be carried out for from about 1 minute to about 3 hours and in one embodiment from about 15 minutes to about 90 minutes. One skilled in the art will understand how the reaction time may vary depending on the reaction conditions and equipment used.

As previously described, the reaction between the hydroxyacetone and the amine compound can result in the formation of an adduct (148). As used herein, "adduct" refers to any chemical species formed by combination or condensation of two or more substances. Presently, the two substances may be hydroxyacetone (134) and an amine compound (144).

The resulting adduct (148) may then be added to a third reactor (150) along with a reducing agent (152) to produce an amino alcohol product (154). The reaction of a carbonyl-containing compound with an amine to form an adduct that is subsequently reduced is known as reductive amination. The reductive amination of aldehyde or ketone-containing compounds may proceed in several steps and by various mechanisms depending on the structure of the reactants and the reaction conditions. See Maschmeyer, T., et al., *Adv. Synth. Catal.* No. 10, 344, 1037-1057 (2002), the disclosure of which is incorporated in its entirety by reference herein. During the reductive amination of hydroxyacetone, the reaction between the hydroxyacetone and the amine compound results in the formation of the adduct (148). In one embodiment, hydroxyacetone may be added gradually to the amine compound in order to maintain low concentrations of hydroxyacetone in the reaction mixture, which upon reduction, could generate propylene glycol thus decreasing the yield of the desired amino alcohol. Also, one skilled in the art would recognize that the reductive amination may be optionally carried out in a single reactor by adding the hydroxyacetone, amine compound, and reducing agent (such as a hydrogenation catalyst and hydrogen) in the same reactor, for example in either the second reactor or the third reactor. In certain embodiments, the reducing agent may be any reducing agent known in the art. For example, suitable reduction reactions include hydrogenation with hydrogen gas and a hydrogenation catalyst, reduction with a hydride source (such as, but not limited to, sodium borohydride, acyloxyborohydrides, triacetoxy borohydride, cyanoborohydrides, and the like), dissolving metal reductions, and aluminum-mercury amalgam reductions. In certain embodiments, the reducing agent (152) may comprise hydrogen gas in the presence of a hydrogenation catalyst, such as a metal hydrogenation catalyst, selected from the group consisting of nickel, cobalt, RANEY® nickel, RANEY® cobalt, RANEY® nickel or RANEY® cobalt doped with other transition metals, nickel oxide, copper, palladium, platinum, rhodium, ruthenium, chromium, iridium, rhenium, molybdenum, iron, manganese, titanium, zirconium, magnesium, oxides thereof, and combinations of any thereof. In specific embodiments, the hydrogenation catalyst may be RANEY® nickel, RANEY® cobalt, or combinations thereof. In certain embodiments, the hydrogenation catalyst may be supported on a material selected from the group consisting of alumina, titania, zirconia, charcoal, chromia, silica, zeolites and combinations of any thereof. The hydrogenation catalyst may be soluble or insoluble and may be dissolved into the reaction mixture or located inside the third reactor (150) as a slurry or packed bed. Although the amount of the hydrogenation catalyst used may vary, in certain embodiments from about 0.01% to about 100% of catalyst may be used and in other embodiment from about 1% to about 20% of catalyst may be used, on a dry weight basis relative to the adduct, for example in a slurry type reactor. For other reactors, such as continuous reactor, for example a fixed bed reactor (including trickle bed reactors), the catalyst loading of the reactor may vary and may depend on the bed reactor design, such as the bed volume of the reactor and/or the reactant flow rate.

According to various embodiments, the reaction conditions at which the adduct can be reduced by the reducing agent may differ. In certain embodiment where the reducing agent (152) comprises hydrogen and the hydrogenation catalyst, the hydrogen may be at a partial pressure of from about 1 bar to about 350 bar, and in other embodiments the hydrogen may be at a partial pressure of from about 10 bar to about 150 bar. According to certain embodiments, the reduction may be carried out at a temperature ranging from about 20° C. to about 250° C. and in other embodiments from about 40° C. to about 85° C. The reaction time may also vary depending on the reducing agent and/or reaction conditions. For example, in certain embodiments, reducing the adduct may occur over from about 1 minute to about 24 hours, and in other embodiments from about 30 minutes to about 6 hours.

According to various embodiments, the third reactor is selected from the group consisting of a batch reactor, a stirred tank reactor, a semi-batch reactor, a continuous reactor, a continuous stirred tank reactor, a slurry reactor, a fixed bed reactor, a tubular reactor, a column reactor, a packed bed reactor, a fluidized bed reactor, a trickle bed reactor, a membrane reactor, a Carberry-type reactor, a plate and frame reactor, a plug flow reactor, and a reactive distillation, or various combinations of any thereof. It will be understood that the manner in which the adduct and reducing agent (such as the hydrogen gas and the hydrogenation catalyst) are fed/added into the reactor can vary depending on the equipment used and the phase of each reaction component.

In one embodiment, the third reactor is a trickle bed reactor. As described herein, in the trickle bed reactor the feed stream (such as the adduct feed stream) is fed into the column at low flow so that a thin layer of the liquid forms over at least a portion of the surface of the hydrogenation catalyst particles (or hydrogenation catalyst on the surface of the support material). When the reducing process is a hydrogenation process, the space between the particles may be fed with the hydrogen gas. While not intending to be limited by any particular mechanism, it is believed that the distance that the hydrogen molecules need to travel from the gas phase to the catalyst surface is through the thin layer of liquid, resulting in efficient mass transfer and an increased reaction rate as compared to other reactor set-ups. The trickle bed reactor may comprise at least one packed column, wherein the column is packed with the hydrogenation catalyst. In certain embodiments, the trickle bed reactor may comprise a plurality of columns packed with the hydrogenation catalyst, such as, for example, from 2 to 10 columns, arranged in series or in parallel. One skilled in the art would recognize that the number of columns in the trickle bed reactor may vary according to the required reaction time, the flow rate of the process, and/or the height, total bed volume, or catalyst loading of the column.

The amino alcohol product (154) may, in addition to an amino alcohol, also comprise any of unreacted adduct, unreacted amine, reducing agent, impurities, water and propylene glycol. Like the previous reactions, the reaction conditions at which the adduct can be reduced by the reducing agent may differ.

Once the amino alcohol product is obtained the various components of the amino alcohol product, as well as the reducing agent, may optionally be further separated from one another in one or more separation processes using any appropriate method known to those skilled in the art. For instance, the reducing agent may be optionally separated (156) from the amino alcohol product and recycled back (158) into the third reactor (150) for reuse. If the reducing agent comprises hydrogen in the presence of a hydrogenation catalyst, the hydrogen may be further separated from the hydrogenation catalyst and both may be recycled back for reuse in later processes (not shown).

Likewise, the amino alcohol product may be separated (160) so as to obtain the individual products (i.e. unreacted adduct (162), unreacted amine (166), impurities (168), water (170), and propylene glycol (172)). For example, streams of unreacted adduct (162), and unreacted amine (166) may be recycled for reuse to save on raw material costs. Water (170), impurities (168) and propylene glycol (172) may be considered byproducts of the reaction and, thus, can be separated and removed from the other reaction products and either processed for further use in another application (propylene glycol), recycled, or disposed (water and impurities). The separation process (160) may include any separation process known in the art, such as, but not limited to, flash distillation, fractional distillation, chromatography, extraction, passing through an acidic resin, and combinations of any thereof. Finally, the amino alcohol (174) may be collected as the desired product for use in a variety of application as, for example as solvents, intermediates for making surface active agents, corrosion inhibitors in metal working fluids, neutralizing agents in acid scrubbing during natural gas or syngas purification processes, and aids in the preparation of compounds in the pharmaceutical industry. As will be understood by those skilled in the art, the specific separation processes used and the degree of separation may depend on the desired purity of the reaction products.

The desired amino alcohol may be a 2-amino-1-propanol. In certain embodiments, the amino alcohol product may be a 2-amino-1-propanol having the general formula:

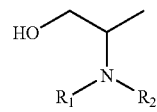

where $R_1$ and $R_2$ are independent of one another and are selected from the group consisting of H, straight-chain or branched-chain $C_1$-$C_{20}$ alkyl (such as methyl, ethyl, n-proyl, isopropyl, n-butyl, isobutyl, sec-butyl, t-butyl, n-pentyl, isopentyl, sec-pentyl, neopentyl, n-hexyl, n-heptyl, n-octyl, 2-ethyl hexyl, n-decyl, n-dodecyl, 2-butyloctyl, n-tridecyl, n-tetradecyl), $C_3$-$C_{20}$ cycloalkyl (for example, $C_3$-$C_8$-cycloalkyl such as cyclopropyl, cyclobutyl, cyclopentyl, cyclohexyl, cycloheptyl, and cyclooctyl), $C_1$-$C_{20}$ hydroxyalkyl (such as 2-hydroxyethyl, 2-hydroxy-n-propyl, 3-hydroxy-n-propyl, 1-hydroxy-methyl-ethyl), aryl (such as phenyl, 1-naphthyl, 2-naphthyl, 1-anthryl, 2-anthryl, and 9-anthryl), $C_7$-$C_{20}$-alkyl-aryl (such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-ethylphenyl, 3-ethylphenyl, 4-ethylphenyl, 2-n-propylphenyl, 3-n-propylphenyl, 4-n-propylphenyl), $C_7$-$C_{20}$-arylalkyl (such as benzyl, 1-phenethyl, 2-phenetyl, 1-phenylpropyl, 2-phenylpropyl, 3-phenylpropyl, 1-phenylbutyl, 2-phenylbutyl, 3-phenylbutyl, 4-phenylbutyl) and mixtures of any thereof. In other embodiments, $R_1$ and $R_2$ may come together to form a heterocyclic ring having from 5 to 7 ring atoms including the nitrogen atom. In view of the processes described herein, one skilled in the art would understand that other structures for groups $R_1$ and $R_2$ are possible depending on the structure of the amine compound used in the optional step of the processes and would be within the scope of the present disclosure as set forth in the claims.

In view of the above, it will be understood that embodiments of the present processes may be carried out using a batch, a semi-batch, or a continuous mode.

Figure 2:
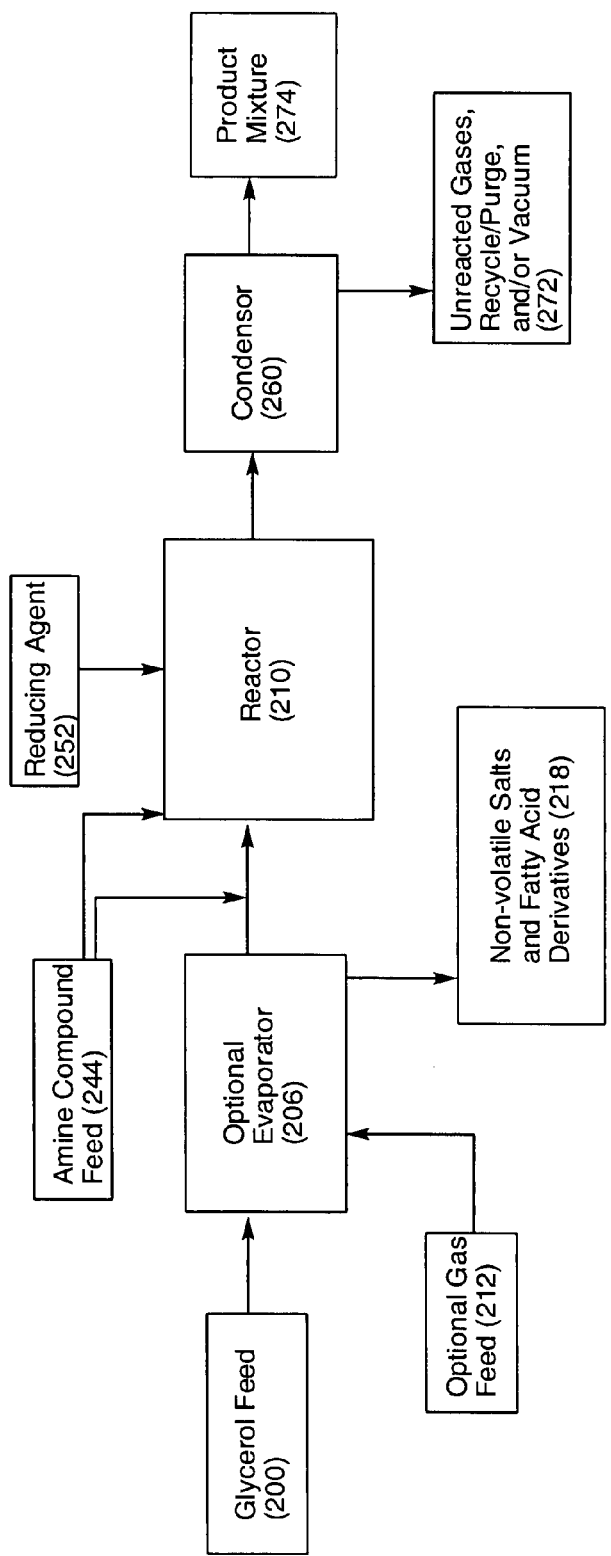
FIG. 2 is a schematic flowchart representing an exemplary embodiment of a one stage process in accordance with the present disclosure.

While certain embodiments of the present disclosure may be described as a two stage process, those skilled in the art will appreciate that the same outcome may be accomplished in a one stage process. Turning now to FIG. 2, wherein the glycerol (200) and optional gas stream (212) are fed to reactor (210). These two streams can optionally pass through evaporator (206) before being fed into reactor (210). Evaporator (206) can remove non-volatile compounds (218) from the glycerol feed. The amine compound (244) is fed either directly into reactor (210) or mixed with the other reactants (200, 212) before entering reactor (210). The reaction from glycerol to hydroxyacetone to the amino alcohol occurs in reactor (210). The crude product mixture is fed to a condenser (260) wherein the desired product mixture (274) is separated from the unreacted gasses and other by-products (272). The feed streams (200, 212, and 244) are the same as those described above with respect to the two stage process of FIG. 1. In certain embodiments, where the amine compound is a gas, such as gaseous ammonia, the amine compound may serve the purpose of gas (212). In other embodiments where the reducing agent (252) is hydrogen and a hydrogenation catalyst, the hydrogen gas may serve the purpose of gas (212). In other embodiments, gas (212) may be a mixture of gas, including a gaseous amine and/or hydrogen. Likewise, the equipment used (206, 210 and 260) can be any of the evaporators, reactors, and condensers described herein. In certain embodiments, the reactor may be a fixed bed reactor, such as a trickle bed reactor, as described herein. In certain embodiment, the fixed bed reactor may contain or be packed with a mixture of the metal catalyst and the hydrogenation catalyst (as described herein). In other embodiments, the metal catalyst and the hydrogenation catalyst may be the same.

The following representative examples are included for purposes of illustration and not limitation.

EXAMPLES

Example 1

About 300 g of refined glycerol (Superol Brand, P&G Chemicals, USA) and about 8.5 g of copper-chromite catalyst (CU-1886P, Engelhard, USA) were weighed out and transferred into a 500 mL reaction flask equipped with a mechanical stirrer, thermocouple, Dean Stark trap/condenser, and gas inlet. The glassware was assembled so that the volatile hydroxyacetone was removed from the reactor as it formed (i.e. $N_2$ gas sparging) and such that samples could be collected as a function of time for later analysis. The reaction components were heated to about 230° C. with constant stirring at about atmospheric pressure. Samples of the resulting hydroxyacetone product were analyzed on an Agilent 6890N Gas Chromatogram using a SPB-1701 30 m×25 mm I.D.× 0.25 µm film column (Supelco). Standards of propylene glycol and hydroxyacetone were used as reference standards. The samples were also analyzed for water content using a model V-200 AquaStar Karl Fisher (EMScience) auto-titrator (freshly calibrated against water). About 238.6 g of hydroxyacetone product was obtained, which contained about 65.9% hydroxyacetone and about 21.7% water. Separation was carried out using fractional distillation under vacuum to yield about 155 g of 90% hydroxyacetone. About 43 g of the hydroxyacetone was charged to a flask and cooled to about 0° C. About 120 mL of 30% aqueous ammonium hydroxide was added to the hydroxyacetone dropwise with stirring while the reaction temperature was maintained below about 10° C. The mixture was stirred for about 60-90 minutes and reaction progress was monitored by gas chromatography. The resulting adduct was charged to a 300 mL Parr reactor along with about 5 g of a nickel catalyst (Actimet M, Engelhard, USA). The reactor was flushed with hydrogen gas, pressurized to about 1100 psig and heated to about 85° C. Reaction progress was monitored at various time points by using an Agilent 6890N Gas Chromatogram using a SPB-1701 30 m×25 mm I.D.×0.25 µm film column (Supelco). Standards of propylene glycol, hydroxyacetone, and 2-amino-1-propanol were run for reference purposes. The reactor was cooled to ambient temperature and the nickel catalyst was separated via filtration to yield about 71.5% of 2-amino-1-propanol.

Example 2

About 375 g of treated glycerol (96% glycerol, P&G Chemicals, USA) and about 11.25 g of copper-chromite catalyst (CU-1886P, Engelhard, USA) were weighed out and transferred into a 500 mL reaction flask equipped with a mechanical stirrer, thermocouple, Dean Stark trap/condenser, and gas inlet. The glassware was assembled so that the volatile hydroxyacetone was removed from the reactor as it formed (i.e. $N_2$ gas sparging). The reaction components were heated to about 230° C. with constant stirring at about atmospheric pressure. Samples of the resulting hydroxyacetone product were collected and analyzed as described in Example 1. About 274.9 g of the hydroxyacetone product (containing about 63.7% hydroxyacetone) was obtained and separated by distillation. About 43 g of the resulting hydroxyacetone (having about 90% purity) was charged to a flask at a temperature of about 10C. About 120 mL of 30% aqueous ammonium hydroxide was added dropwise with stirring while the reaction temperature is maintained at about 10° C. The mixture was stirred for about 60-90 minutes and reaction progress was monitored by gas chromatography. The resulting adduct was then charged to a 300 mL Parr reactor along with about 10 g of nickel catalyst (Actimet M, Engelhard, USA). The reactor was flushed with hydrogen gas, pressurized to about 1100 psig and heated to about 85° C. Reaction progress was monitored by gas chromatography as described in Example 1. The reactor was cooled to about ambient temperature and the nickel catalyst was separated from the amino alcohol product via filtration to yield about 84.6% of 2-amino-1-propanol.

Example 3

About 88 g of crude glycerol (88.7% glycerol, Twin Rivers Technologies, USA) was flashed over into a 500 mL reaction flask equipped with a mechanical stirrer, thermocouple, Dean Stark trap/condenser, and gas inlet. About 9 g of copper-chromite catalyst (CU-1886P, Engelhard, USA) was added to the reactor. The glassware was assembled so that the volatile hydroxyacetone was removed from the reactor as it formed (i.e. $N_2$ gas sparging). Samples of the resulting hydroxyacetone product were collected and analyzed as described in Example 1. About 207.9 g of the hydroxyacetone product (containing about 49.8% hydroxyacetone) was obtained. About 50 g of the hydroxyacetone product was then charged to a flask and about 61 mL of 30% aqueous ammonium hydroxide was added dropwise with stirring at about room temperature. The mixture was stirred for about 90 minutes and reaction progress was monitored using gas chromatography. The resulting adduct was charged to a 300 mL Parr reactor along with about 6 g of a nickel catalyst (Actimet M, Engelhard, USA). The reactor was flushed with hydrogen gas, pressurized to about 1100 psig and heated to a temperature of about 85° C. Reaction progress was monitored by gas chromatography as described in Example 1. The reactor was cooled to ambient temperature and the nickel catalyst was separated from the resulting amino alcohol product via filtration to yield about 83.5% of 2-amino-1-propanol.

Example 4

About 299 g of refined glycerol (Superol Brand, P&G Chemicals, USA) and about 8.5 g of copper-chromite catalyst (CU-1955P, Engelhard, USA) were weighed out and transferred into a 500 mL reaction flask. The flask was equipped with a mechanical stirrer, thermocouple, Dean Stark trap/condenser, and gas inlet. The glassware was assembled so that the volatile hydroxyacetone was removed from the reactor as it formed (i.e. $N_2$ gas sparging is used). Samples of the resulting hydroxyacetone product were collected and analyzed as described in Example 1. About 235 g of the hydroxyacetone product was obtained and was determined to contain about 59.4% hydroxyacetone. The hydroxyacetone product was separated using fractional distillation under vacuum to yield about 150 g of 90% hydroxyacetone, about 95 g of which was then charged to a flask. Ammonia gas (Mattheson Tri Gas, USA) was slowly bubbled through the hydroxyacetone for about 30 minutes while keeping the temperature at or below about 20° C., followed by stirring for an additional 30 minutes. Reaction progress was monitored by gas chromatography. The resulting adduct was charged to a 300 mL Parr reactor along with about 18 g of a nickel catalyst (Actimet M, Engelhard, USA). The reactor was flushed with hydrogen gas, pressurized to about 1100 psig and heated to a temperature of about 85° C. Reaction progress was monitored by gas chromatography as described in Example 1. The reactor was cooled to ambient temperature and the nickel catalyst was separated from the resulting amino alcohol product via filtration to yield about 33.4% of 2-amino-1-propanol.

Example 5

In this Example, hydroxyacetone was converted to 2-amino-1-propanol using a nickel oxide hydrogenation catalyst. Hydroxyacetone (36.71 g, 0.50 mol) was charged to a 250 mL round bottom flask at room temperature. Ammonium hydroxide (100 mL, 1.48 mol) was dropwise added with stirring. The reaction was stirred for a total time of 90 minutes. Progress was monitored by GC. The resulting adduct solution was charged to a 300 mL Parr reactor along with nickel oxide on kieselguhr (Sud-Chemie, G-49B RS: 1.52 g, 1.1 wt %). The reactor was flushed four times with $H_2$, pressurized with $H_2$ to 151.7 bar, and heated to 85° C. with stirring at 1500 rpm using a gas entrainment impeller. Reaction progress was monitored by gas chromatography as described in Example 1. The reactor was cooled to ambient temperature and the catalyst was separated via filtration to yield 2-amino-1-propanol with a conversion of 96% and a selectivity of 98%.

Example 6

In this Example, hydroxyacetone was converted to 2-amino-1-propanol using a nickel oxide hydrogenation catalyst at lower hydrogen pressure. Hydroxyacetone (36.92 g, 0.50 mol) was charged to a 250 mL round bottom flask at room temperature. Ammonium hydroxide (100 mL, 1.48 mol) was dropwise added with stirring. The reaction was stirred for a total time of 90 minutes. Progress was monitored by GC. The resulting adduct solution was charged to a 300 mL Parr reactor along with nickel oxide on kieselguhr (Sud-Chemie, G-49B RS: 1.55 g, 1.1 wt %). The reactor was flushed four times with $H_2$, pressurized with $H_2$ to 34.5 bar, and heated to 85° C. with stirring at 1500 rpm using a gas entrainment impeller. Reaction progress was monitored by gas chromatography as described in Example 1. The reactor was cooled to ambient temperature and the catalyst was separated via filtration to yield 2-amino-1-propanol with a conversion of 92% and a selectivity of 73%.

Example 7

In this Example, hydroxyacetone was converted to a product mixture comprising propylene glycol and 2-amino-1-propanol in a batch-type process. Hydroxyacetone (98.91 g, 1.34 mol) was charged to a 250 mL round bottom flask at room temperature. Ammonium hydroxide (46.0 mL, 0.68 mol) was dropwise added with stirring. The reaction was stirred for a total time of 90 minutes. Progress was monitored by GC. The resulting adduct solution was charged to a 300 mL Parr reactor along about 5 g of a nickel catalyst (Actimet M, Engelhard, USA). The reactor was flushed with $H_2$, pressurized with $H_2$ to 151.7 bar and heated to 85° C. with stirring at 1500 rpm using a gas entrainment impeller. Reaction progress was monitored by gas chromatography as described in Example 1. The reactor was cooled to ambient temperature and the catalyst was separated via filtration to yield a product mixture comprising 2-amino-1-propanol (17.9%) and propylene glycol (30.7%).

Example 8

In this Example, hydroxyacetone was converted to propylene glycol in a batch-type process. Crude hydroxyacetone, 70 g, (obtained as described in Example 1) was charged to a 300 mL Parr reactor along 0.5 g of a Ru/C catalyst (Aldrich Chemicals, Milwaukee, Wis.). The reactor was flushed with $H_2$ several times, pressurized with $H_2$ to 10.3 bar and heated to 120° C. under vigorous stirring for 3 hrs. The reactor was then cooled to ambient temperature and the catalyst was separated via filtration to yield the product mixture with a composition according to Table 1.

TABLE 1

Product Mixture from Reduction of Hydroxyacetone

| Wt. % Component | Crude Hydroxyacetone | Reaction Product |
|---|---|---|
| Hydroxyacetone | 63.9 | 4.0 |
| Propylene Glycol | 3.0 | 67.6 |
| Water | 19.6 | 21.6 |

TABLE 1-continued

Product Mixture from Reduction of Hydroxyacetone

| Wt. % Component | Crude Hydroxyacetone | Reaction Product |
|---|---|---|
| Glycerol | 1.2 | 3.1 |
| By-Products | 12.3 | 3.8 |

Example 9

In this Example, glycerol was converted to propylene glycol via a single stage (on reactor) reaction. Glycerol (100 g, 1.1 mol) was charged to a 300 mL Parr reactor along 5 g of a copper chromite catalyst (CU-1886P, Engelhard, USA). The reactor was flushed with $H_2$ several times, pressurized with $H_2$ to 103.4 bar, and heated to 230° C. with stirring at 550 rpm. Reaction progress was monitored by gas chromatography. After 21 hrs, the reactor was cooled to ambient temperature and the catalyst was separated via filtration to yield a product mixture containing 55% glycerol, 35% propylene glycol, 3.9% propanol, and other impurities such as ethylene glycol, methanol, and ethanol.

Example 10

In this Example, hydroxyacetone was reacted with ammonium hydroxide to give the adduct which was converted to 2-amino-1-propanol using a trickle bed reactor. Hydroxyacetone (37.33 g, 0.50 mol) was charged to a 250 mL round bottom flask at room temperature. Ammonium hydroxide (100 mL, 1.48 mol) was dropwise added with stirring. The reaction was stirred for a total time of 90 minutes. Progress was monitored by GC. The adduct was submitted to the trickle bed reactor.

A trickle bed reactor with a length of 37.9 cm and an internal diameter 2.54 cm was used. The adduct solution was fed to the reactor via an HPLC pump. The catalyst used was a RANEY® Nickel catalyst (Raney 5886, commercially available from GRACE Davison) supplied in the form of particles. The $H_2$ pressure in the reactor was 31.0 bar. The reaction was conducted in three runs changing the residence time in the reactor, the hydrogen:adduct ratio, the feed flow rate and the gas flow rate. The conditions for each run are presented in Table 2. Product samples from the reactor were condensed and were analyzed on a Agilent 6890N Gas Chromatogram using a SPB-1701 30 m×25 mm I.D.×0.25 μm film column (available from Supelco). The results of the three runs are presented in Table 3.

TABLE 2

Reaction Conditions

| Example | 10.1 | 10.2 | 10.3 |
|---|---|---|---|
| Inlet Temperature ° C. | 85 | 85 | 85 |
| Column Temperature ° C. | 85 | 85 | 85 |
| Pressure, bar | 31.0 | 31.0 | 31.0 |
| Residence Time, s | 1200 | 2400 | 600 |
| Hydrogen: Adduct ratio | 8 | 16 | 16 |
| Feed Flow Rate (mL/min) | 0.5 | 0.25 | 1.0 |
| Gas Flow Rate (sccm) | 49.8 | 49.8 | 102.6 |

TABLE 3

Results for Trickle Bed Production of 2-Amino-1-Propanol

| Example | 10.1 | 10.2 | 10.3 |
|---|---|---|---|
| % Adduct | 38.9 | 25.1 | 63.4 |
| % 2-Amino-1-propanol | 58.8 | 60.8 | 29.7 |
| % Hydroxyacetone | 2.3 | 3.6 | 2.9 |
| % Propylene glycol | 0 | 0 | 0 |
| % Other | 0 | 10.5 | 4 |

Example 11

In this Example a trickle bed reactor is used to convert hydroxyacetone to propylene glycol. A trickle bed reactor with a length of 37.9 cm and an internal diameter of 2.54 cm is used. A hydroxyacetone solution containing 20 wt. % water is fed to the reactor via an HPLC pump. The catalyst used is a Raney Nickel catalyst (Raney 5886, commercially available from GRACE Davison) supplied in the form of particles. Reaction conditions used are presented in Table 4. Product samples from the reactor are condensed and are analyzed on a Agilent 6890N Gas Chromatogram using a DB-1 25 m×0.53 mm I.D.×5.00 micron column (available from J & W Scientific. Catalog # 1251025).

Analysis of the organic constituents by GC of the reaction product shows a mixture comprising propylene glycol, hydroxyacetone, and water. The water and hydroxyacetone are evaporated from the product using a laboratory rotary vacuum dryer, leaving a final product comprising propylene glycol.

TABLE 4

Reaction Conditions

| Feed | Purified Hydroxyacetone (>99%) |
|---|---|
| Pressure | about 31.0 bar |
| Temperature | about 85° C. |
| Hydrogen Flow Rate | about 90 sccm |
| Feed Flow Rate | about 0.5 mL/min |

Example 12

In this Example, a trickle bed reactor is used to convert hydroxyacetone to a product mixture comprising propylene glycol and 2-amino-1-propanol via the adduct intermediate. A trickle bed reactor with a length of 37.94 cm and an internal diameter of 2.54 cm and containing about 190 cc of catalyst is prepared. The catalyst is a RANEY® Nickel catalyst (Raney 5886, commercially available from GRACE Davison) supplied in the form of particles Hydroxyacetone solution is fed to the reactor via an HPLC pump. Product samples from the reactor were condensed and were analyzed on a Agilent 6890N Gas Chromatogram using a DB-1 25 m×0.53 mm I.D.×5.00 micron column (available from J & W Scientific. Catalog # 1251025). The reaction conditions are presented in Table 5.

Analysis of the organic constituents by GC of the reaction product shows a mixture of 2-amino-1-propanol, propylene glycol, hydroxyacetone, and water. The water and hydroxyacetone are evaporated from the product using a laboratory rotary vacuum dryer, leaving a final product composed of 2-amino-1-propanol and propylene glycol.

TABLE 5

Reaction Conditions

| Feed | Purified Hydroxyacetone (>99%) |
|---|---|
| Pressure | about 31.0 bar |
| Temperature | about 85° C. |
| Hydrogen Flow Rate | about 90 sccm |
| Ammonia Flow Rate | about 10 sccm |
| Feed Flow Rate | about 0.5 mL/min |

Example 13

In this Example, glycerol was converted to propylene glycol using a trickle bed reactor. The reactor used for the continuous version of this process was a trickle bed reactor with a length of 37.94 cm and an internal diameter of 2.54 cm and containing 190 cc of catalyst. The catalyst used was a copper chromite catalyst (CU-1808 T ⅛, commercially available from Engelhard) in the form of 3.2 mm extruded pellets.

The catalyst, once loaded, was first activated by the supply of a stream of 100% nitrogen to the reactor with heating until the reactor reached the desired activation temperature of 130° C. The stream of nitrogen gas was then replaced by a stream including 98% by volume of nitrogen and 2% by volume of hydrogen, and conditions were maintained until no exotherm was noted in catalyst bed. During this operation, which lasts for several hours, it was important to prevent the temperature from exceeding 170° C. The hydrogen was incrementally increased (2, 5, 10, 25, 50, 100%) until the stream was solely hydrogen.

Fifteen runs were conducted while varying the reaction conditions (temperature, glycerol flow rate, hydrogen flow rate, molar ratio of hydrogen to glycerol, and residence time within the reactor). Reaction Conditions for the various runs are listed in Table 6. Product samples were analyzed on an Agilent 6890N Gas Chromatogram using a DB-1 25 m×0.53 mm I.D.×5.00 micron column (available from J & W Scientific. Catalog # 1251025). The compositions of the product mixture for each of the fifteen runs are listed in Table 7.

TABLE 6

Reaction Conditions

| Run # | Temp (° C.) | Pressure (bar) | Glycerol Flow Rate (mL/min) | $H_2$ Flow Rate (sccm) | Mole Ratio ($H_2$:Gly) | Residence Time (min) |
|---|---|---|---|---|---|---|
| 1 | 200 | 32.0 | 0.5 | 36 | 4 to 1 | 15 m |
| 2 | 200 | 32.0 | 0.5 | 178.3 | 20 to 1 | 15 m |
| 3 | 200 | 32.0 | 0.5 | 356.5 | 40 to 1 | 15 m |
| 4 | 200 | 32.0 | 0.12 | 11.14 | 5 to 1 | 60 m |
| 5 | 200 | 32.0 | 0.25 | 34.3 | 10 to 1 | 30 m |
| 6 | 200 | 32.0 | 0.25 | 76.25 | 20 to 1 | 30 m |
| 7 | 200 | 32.0 | 0.5 | 73.025 | 10 to 1 | 15 m |
| 8 | 180 | 32.0 | 0.25 | 36.51 | 10 to 1 | 30 m |
| 9 | 220 | 32.0 | 0.25 | 36.51 | 10 to 1 | 30 m |
| 10 | 220 | 32.0 | 0.25 | 109.54 | 30 to 1 | 30 m |
| 11 | 180 | 32.0 | 0.75 | 36.51 | 3.33 to 1 | 10 m |
| 12 | 180 | 32.0 | 0.25 | 109.54 | 30 to 1 | 30 m |
| 13 | 220 | 32.0 | 0.75 | 36.51 | 3.33 to 1 | 10 m |
| 14 | 180 | 32.0 | 0.75 | 109.54 | 10 to 1 | 10 m |
| 15 | 220 | 32.0 | 0.75 | 109.54 | 10 to 1 | 10 m |

TABLE 7

Results for Trickle Bed Production of Propylene Glycol

| | GC Data by Wt. % | | | |
|---|---|---|---|---|
| Run # | % PG | % HA | % Gly | % Other |
| 1 | 37.8% | 1.9% | 52.8% | 7.5% |
| 2 | 41.2% | 2.8% | 44.8% | 11.2% |
| 3 | 38.8% | 2.2% | 51.2% | 7.8% |
| 4 | 62.4% | 8.9% | 18.3% | 10.4% |
| 5 | 72.4% | 5.6% | 10.3% | 11.8% |
| 6 | 62.4% | 9.2% | 19.9% | 8.5% |
| 7 | 38.9% | 1.6% | 40.3% | 19.2% |
| 8 | 35.3% | 8.4% | 29.6% | 26.6% |
| 9 | 49.6% | 6.1% | 12.8% | 31.5% |
| 10 | 45.7% | 2.9% | 22.7% | 28.7% |
| 11 | 13.0% | 2.9% | 70.1% | 13.9% |
| 12 | 26.5% | 6.6% | 24.5% | 42.4% |
| 13 | 36.8% | 5.6% | 16.2% | 41.3% |
| 14 | 11.7% | 0.8% | 76.3% | 11.3% |
| 15 | 36.0% | 3.6% | 21.9% | 38.5% |

PG = propylene glycol, HA = hydroxyacetone, Gly = glycerol

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for converting glycerol to an amino alcohol product comprising:
   reacting glycerol with a metal catalyst to obtain hydroxyacetone;
   reacting the hydroxyacetone with an amine compound to obtain an adduct; and
   reducing the adduct using a reducing agent to obtain an amino alcohol product.

2. The process of claim 1, wherein the metal catalyst is a catalyst selected from the group consisting of copper, chromium, nickel, zinc, cobalt, manganese, silicon, aluminum, copper chromite, copper zinc, oxides thereof, and combinations of any thereof.

3. The process of claim 1, wherein reacting the glycerol with the metal catalyst occurs at a temperature of from about 160° C. to about 300° C.

4. The process of claim 1, wherein reacting the glycerol with the metal catalyst occurs under gas sparging.

5. The process of claim 1, wherein reacting the glycerol with the metal catalyst occurs at a pressure of from about 0.1 bar to about 60 bar.

6. The process of claim 1, wherein the reducing agent comprises hydrogen in the presence of a hydrogenation catalyst selected from the group consisting of nickel, cobalt, RANEY® nickel, RANEY® cobalt, RANEY® nickel or RANEY® cobalt doped with other transition metals, nickel oxide, copper, palladium, platinum, rhodium, ruthenium, chromium, iridium, rhenium, manganese, molybdenum, iron, titanium, zirconium, magnesium, oxides thereof, and combinations of any thereof.

7. The process of claim 6, wherein the hydrogen is at a pressure of from about 1 bar to about 350 bar.

8. The process of claim 6, wherein the hydrogenation catalyst is supported on a material selected from the group consisting of alumina, titania, zirconia, charcoal, chromia, silica, zeolites, and combinations of any thereof.

9. The process of claim 1, wherein the amine compound is a compound selected from the group consisting of ammonia, ammonium hydroxide, hydroxylamine, primary amines, secondary amine, alkanolamines and combinations of any thereof.

10. The process of claim 1, wherein adduct is reduced using a reducing agent at a temperature of from about 20° C. to about 250° C.

11. The process of claim 1, wherein reacting glycerol with the metal catalyst to obtain hydroxyacetone occurs in a first reactor and wherein the hydroxyacetone is transferred to one or more other reactors to complete the reaction to the amino alcohol product.

12. The process of claim 11, wherein the first reactor is a trickle bed reactor.

13. The process of claim 1, wherein reducing the adduct using a reducing agent occurs in a trickle bed reactor.

14. The process of claim 1, wherein reacting glycerol with the metal catalyst occurs in a first trickle bed reactor and reducing the adduct using a reducing agent occurs in a second trickle bed reactor.

15. The process of claim 1, wherein reacting glycerol with the metal catalyst to obtain hydroxyacetone occurs in a first reactor and the hydroxyacetone is converted to the amino alcohol product in the first reactor.

16. The process of claim 15, wherein the first reactor is a trickle bed reactor.

17. The process of claim 1, wherein the glycerol is fed into a first reactor in one of a liquid phase and a gaseous phase.

18. A process for converting glycerol to an amino alcohol product comprising:
reacting glycerol with a metal catalyst at a temperature of from about 160° C. to about 300° C. to obtain hydroxyacetone;
reacting the hydroxyacetone with an amine compound at a temperature of from about −20° C. to about 150° C. to obtain an adduct; and
reducing the adduct using a reducing agent at a temperature of from about 20° C. to about 250° C. to obtain an amino alcohol product.

19. The process of claim 18, wherein the metal catalyst is a catalyst selected from the group consisting of copper, chromium, nickel, zinc, cobalt, manganese, silicon, aluminum, copper chromite, copper zinc, oxides thereof, and combinations of any thereof.

20. The process of claim 18, the reducing agent comprises hydrogen in the presence of a hydrogenation catalyst selected from the group consisting of nickel, cobalt, RANEY® nickel, RANEY® cobalt, RANEY® nickel or RANEY® cobalt doped with other transition metals, nickel oxide, copper, palladium, platinum, rhodium, ruthenium, chromium, iridium, rhenium, manganese, molybdenum, iron, titanium, zirconium, magnesium, oxides thereof, and combinations of any thereof.

21. The process of claim 18, wherein the amine compound is a compound selected from the group consisting of ammonia, ammonium hydroxide, hydroxylamine, primary amines, secondary amine, alkanolamines and combinations of any thereof.

22. A process for converting glycerol to an amino alcohol having the formula:

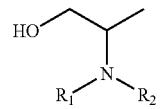

the process comprising:
reacting glycerol with a metal catalyst at a temperature of from about 160° C. to about 300° C. to obtain hydroxyacetone;
reacting the hydroxyacetone with an amine compound at a temperature of from about −20° C. to about 150° C. to obtain an adduct; and
reducing the adduct using a reducing agent at a temperature of from about 20° C. to about 250° C. to obtain an amino alcohol product
wherein $R_1$ and $R_2$ are independent of one another and are selected from the group consisting of H, $C_1$-$C_{20}$ alkyl, $C_3$-$C_{20}$ cycloalkyl, $C_1$-$C_{20}$ hydroxyalkyl, aryl, $C_7$-$C_{20}$ alkyl-aryl, $C_7$-$C_{20}$ aryl-alkyl, and mixtures thereof or $R_1$ and $R_2$ come together with the nitrogen to form a heterocyclic ring having from 5 to 7 ring atoms.

23. The process of claim 22, wherein the metal catalyst is a catalyst selected from the group consisting of copper, chromium, nickel, zinc, cobalt, manganese, silicon, aluminum, copper chromite, copper zinc, oxides thereof and combinations of any thereof; and
the reducing agent comprises hydrogen in the presence of a hydrogenation catalyst selected from the group consisting of nickel, cobalt, RANEY® nickel, RANEY® cobalt, RANEY® nickel or RANEY® cobalt doped with other transition metals, nickel oxide, copper, palladium, platinum, rhodium, ruthenium, chromium, iridium, rhenium, manganese, molybdenum, iron, titanium, zirconium, magnesium, oxides thereof, and combinations of any thereof.

* * * * *